United States Patent
Shiraishi et al.

(10) Patent No.: US 9,920,399 B2
(45) Date of Patent: *Mar. 20, 2018

(54) TITANIUM ALLOY MEMBER AND PRODUCTION METHOD THEREFOR

(75) Inventors: Tohru Shiraishi, Yokohama (JP); Yoshiki Ono, Yokohama (JP); Yuji Araoka, Yokohama (JP)

(73) Assignee: NHK SPRING CO., LTD., Kanagawa (JP)

( * ) Notice: Subject to any disclaimer, the term of this patent is extended or adjusted under 35 U.S.C. 154(b) by 78 days.

This patent is subject to a terminal disclaimer.

(21) Appl. No.: 14/123,620

(22) PCT Filed: Apr. 27, 2012

(86) PCT No.: PCT/JP2012/061783
§ 371 (c)(1),
(2), (4) Date: Dec. 3, 2013

(87) PCT Pub. No.: WO2012/169304
PCT Pub. Date: Dec. 13, 2012

(65) Prior Publication Data
US 2014/0112819 A1    Apr. 24, 2014

(30) Foreign Application Priority Data

Jun. 9, 2011 (JP) ................................. 2011-128984

(51) Int. Cl.
C22C 14/00 (2006.01)
C23C 8/24 (2006.01)
(Continued)

(52) U.S. Cl.
CPC .............. *C22C 14/00* (2013.01); *A61L 27/06* (2013.01); *B22F 1/0088* (2013.01); *B22F 3/10* (2013.01);
(Continued)

(58) Field of Classification Search
CPC .. B22F 1/0081; B22F 1/88; B22F 3/24; C22F 1/183; C22C 1/0458; C22C 14/00; A61L 27/06
(Continued)

(56) References Cited

U.S. PATENT DOCUMENTS 4,898,624 A * 2/1990 Chakrabarti et al. ......... 420/420
5,759,484 A    6/1998 Kashii et al.
(Continued)

FOREIGN PATENT DOCUMENTS

EP    2719781 A1    4/2014
JP    H02-232303 A    9/1990
(Continued)

OTHER PUBLICATIONS

Itoh, et al, "Improving the tribological properties of Ti-6Al-4V alloy by nitrogen-ion implantation," Surface and Coatings Technology 111 (1999), pp. 172-176.*
(Continued)

*Primary Examiner* — Keith Walker
*Assistant Examiner* — John A Hevey
(74) *Attorney, Agent, or Firm* — Oliff PLC

(57) ABSTRACT

A titanium alloy member with high strength and high proof stress not only in the surface but also inside, using a general and inexpensive α-β type titanium alloy, and a production method therefor, are provided. The production method includes preparing a raw material made of titanium alloy, nitriding the raw material to form a nitrogen-containing raw material by generating a nitrogen compound layer and/or a nitrogen solid solution layer in a surface layer of the raw material, mixing the raw material and the nitrogen-containing raw material to yield a nitrogen-containing mixed material, sintering the nitrogen-containing mixed material to obtain a sintered titanium alloy member by bonding the (Continued)

Picture 1 Sample 104

Picture 2 Comparative sample 10

Picture 3 Comparative sample 11 material together and uniformly diffusing nitrogen in solid solution from the nitrogen-containing raw material to the entire interior portion of the sintered titanium alloy member, and hot plastic forming the sintered titanium alloy member.

14 Claims, 4 Drawing Sheets

(51) Int. Cl.
  *C23C 8/80* (2006.01)
  *C22F 1/18* (2006.01)
  *B22F 3/10* (2006.01)
  *B22F 1/00* (2006.01)
  *B22F 3/14* (2006.01)
  *C22C 1/04* (2006.01)
  *A61L 27/06* (2006.01)
  *B22F 3/03* (2006.01)
  *B22F 3/20* (2006.01)

(52) U.S. Cl.
  CPC ............. *B22F 3/14* (2013.01); *C22C 1/0458* (2013.01); *C22F 1/183* (2013.01); *C23C 8/24* (2013.01); *C23C 8/80* (2013.01); *B22F 3/03* (2013.01); *B22F 2003/208* (2013.01); *B22F 2998/10* (2013.01); *B22F 2999/00* (2013.01)

(58) Field of Classification Search
  USPC ........ 419/30, 32, 34, 57; 420/417, 418, 420, 420/421
  See application file for complete search history.

(56) References Cited

U.S. PATENT DOCUMENTS

| | | | |
|---|---|---|---|
| 6,063,211 | A | 5/2000 | Soeda et al. |
| 7,416,697 | B2 * | 8/2008 | Woodfield et al. ............. 419/38 |
| 7,442,266 | B2 * | 10/2008 | Furuta et al. ................. 148/421 |
| 2006/0099432 | A1 | 5/2006 | Keener |
| 2007/0193662 | A1 * | 8/2007 | Jablokov et al. ............. 148/421 |
| 2011/0027043 | A1 | 2/2011 | Keener |
| 2012/0168042 | A1 * | 7/2012 | Lee et al. ..................... 148/557 |
| 2014/0212319 | A1 * | 7/2014 | Shiraishi et al. ............... 419/13 |

FOREIGN PATENT DOCUMENTS

| | | | |
|---|---|---|---|
| JP | A-05-272526 | | 10/1993 |
| JP | H07-41806 A | | 2/1995 |
| JP | A-08-157987 | | 6/1996 |
| JP | H11-140557 A | | 5/1999 |
| JP | A-2000-096208 | | 4/2000 |
| JP | A-2007-113120 | | 5/2007 |
| JP | 2009-052993 A | | 3/2009 |
| JP | B2-4303821 | | 7/2009 |
| WO | WO 96/33292 A1 | | 10/1996 |
| WO | WO 2011/037127 | * | 3/2011 |
| WO | 2012169305 A1 | | 12/2012 |

OTHER PUBLICATIONS

International Search Report issued in Application No. PCT/JP2012/061783; dated Aug. 14, 2012 (With Translation).
Jan. 30, 2015 Extended Search Report issued in European Application No. 12797338.6.
Mar. 24, 2015 Office Action issued in Japanese Patent Application No. 2011-128984.

* cited by examiner

Picture 1 Sample 104

Picture 2 Comparative sample 10

Picture 3 Comparative sample 11

TITANIUM ALLOY MEMBER AND PRODUCTION METHOD THEREFOR

TECHNICAL FIELD

The present invention relates to an titanium alloy member having high strength and high proof stress used in parts that are required to be light in weight and have high strength, and relates to a production method therefor.

BACKGROUND ART

Titanium alloys are light in weight and have high strength and are therefore used in various fields of parts in which low weight is important, such as aircraft parts and automobile parts. Titanium alloys are also superior in corrosion resistance and biocompatibility and are also widely used in the field of biological implant devices. In any of these fields, α-β type titanium alloys, typically exemplified by Ti-6Al-4V, are common because the alloys have high strength and broad utility.

In view of these circumstances, development of increased strength in α-β type titanium alloys that have high practical utility due to low cost are actively pursued. For example, patent publication No. 1 below discloses a technique in which Ti-6Al-4V is subjected to gas nitriding, and a brittle TiN compound surface layer is removed, thereby improving fatigue strength. Patent publication No. 2 below discloses a technique in which a first layer of a nitrogen solid solution hard layer and a second layer of an oxygen solid solution hard layer are formed simultaneously on pure titanium or Ti-6Al-4V, thereby hardening a surface of the member. Patent publication No. 3 below discloses a composite material in which a TiC compound is dispersed in Ti-6Al-4V.

On the other hand, β type titanium alloy can be mentioned as the high strength titanium alloy. However, the β type titanium alloy contains a great amount of rare metals and is more expensive than the α-β type titanium alloys. Furthermore, in the β type titanium alloy, the static strength can be improved by age (precipitation) hardening, but the fatigue strength is not proportional to the static strength and is not sufficiently improved. This is because precipitated phase with high hardness is generated by the age hardening treatment and improves the static strength, but has a great difference in the hardness (or elastic strain) from the matrix primarily made of the β phase. Thus, for fatigue caused by repeated stresses, a boundary between the precipitated phase and the β phase tends to be origins of fractures.

The above-mentioned patent publications are as follow.
1: Japanese Unexamined Patent Application Laid-Open No. Hei5 (1993)-272526
2: Japanese Unexamined Patent Application Laid-Open No. 2000-96208
3: Japanese Patent No. 4303821

According to the techniques disclosed in the patent publications Nos. 1 and 2, only the surface of the member is strengthened, and the inside of the member is difficult to strengthen. That is, the techniques are effective for improving wear resistance and preventing fatigue crack formation on the surface, but are less effective for improving static strength and preventing fatigue crack growth. In the technique disclosed in the patent publication No. 3, a titanium alloy powder and a TiC compound powder are mixed together, compacted, and then sintered. It is difficult to uniformly mix powders which have different specific gravity, and the metallic structure after the sintering is therefore not uniform. That is, low-strength portions may exist and decrease reliability of strength as a member and quality stability, and thereby the sintered compact is difficult to produce as industrial products practically.

In the technique disclosed in the patent publication No. 2, the alloy contains a second layer of an oxygen solid solution hard layer in which oxygen is an α-stabilizing element as well as nitrogen. Although oxygen is an α-stabilizing element as well as nitrogen, oxygen easily forms a hard and brittle α case (α-stabilizing element rich layer) compared to nitrogen. Therefore, it is difficult to stably control the formation of the oxygen solid solution hard layer in a production process. It is generally known that the action of oxygen for high strengthening is less than that of nitrogen.

SUMMARY OF THE INVENTION

As described above, although development of highly strengthened titanium alloys by utilizing nitrogen has been made, there has not been provided a technique in which a member is highly strengthened in the entirety to the interior portion. There is little research regarding proof stress (or yield strength) that is an index of practical strength (that is, fatigue strength) of parts to be subjected to repeated stresses, although research is performed regarding high strength. In view of these circumstances, an object of the present invention is to provide a titanium alloy member that is made of an inexpensive α-β type titanium alloy having broad utility and has high proof stress and high strength from the surface to the entire interior portion, and a production method therefor.

The present invention provides a method for producing a titanium alloy member, the method including: preparing a raw material made of titanium alloy; nitriding the raw material to form a nitrogen-containing raw material by generating a nitrogen compound layer and/or a nitrogen solid solution layer in a surface layer of the raw material; mixing the raw material and the nitrogen-containing raw material to yield a nitrogen-containing mixed material; sintering the nitrogen-containing mixed material to obtain a sintered titanium alloy member by bonding the material together and uniformly diffusing nitrogen in solid solution from the nitrogen-containing raw material to the entire interior portion of the sintered titanium alloy member; and hot plastic forming the sintered titanium alloy member.

According to the present invention, the sintering process yields a sintered titanium alloy member in which nitrogen contained in the nitrogen-containing raw material uniformly diffuses to the entire interior portion of the sintered body by solid solution. It should be noted that the sintered titanium alloy member is then subjected to hot plastic forming, whereby a titanium alloy member that is highly strengthened overall and that has high proof stress is obtained. When nitrogen compounds such as TiN compound are formed, difference in hardness (or elastic strain) between the highly hardened TiN compound phase and the matrix is large, and the boundary thereof is easily the origin of fractures in fatigue in which repeated stress is loaded. On the other hand, in the present invention, nitrogen is contained in solid solution, and there is no boundary having a large difference in hardness and readily being an origin of fractures between the highly hardened phase such as a nitrogen compound and the matrix, whereby fatigue resistance is improved.

The material for the raw material of the present invention is preferably a widely used α-β type titanium alloy. Examples of the material may include Ti-3Al-2.5V, Ti-3Al-3Mo-1V, Ti-4Al-3Mo-1V, Ti-4Al-4Mo-2Sn, Ti-5Al-2Cr-1Fe, Ti-5Al-1.5Fe-1.5 Cr-1.5Mo, Ti-5Al-2Sn-2Zr-4Mo-4Cr, Ti-6Al-2Sn-2Zr-2Mo-2Cr, Ti-6Al-2Sn-4Zr-6Mo, Ti-6Al- 2Sn-4Zr-2Mo, Ti-5Al-6Sn-2Zr-1Mo, Ti-6Al-2Cb-1Ta-1Mo, Ti-6Al-4V, Ti-6Al-6V-2Sn, Ti-7Al-4V, Ti-8Al-1Mo-1V, Ti-8Al-4Co, Ti-8Mn, and Ti-25Al-11Sn-5Zr-1Mo.

Powders, thin strips, thin pieces, and fibers may be used for the raw material. Among these forms, thin strips, thin pieces, and fibers are preferable in view of handling and safety. These forms can easily be the same size, whereby control of amount of nitrogen in the nitriding, that is, control of amount of nitrogen contained in a sintered titanium alloy member can be easy, and therefore, thin strips, thin pieces, and fibers are preferable to powders. Fibers that are obtained by production methods for woven cloth and unwoven cloth are more preferable to thin strips and thin pieces. The production methods for woven cloth and unwoven cloth enable a more uniform mixing of a raw material and a nitrogen-containing raw material, whereby nitrogen can easily diffuse more uniformly to a sintered titanium alloy member overall. As for the method of producing fibers, a molten metal extraction method is most suitable because titanium alloy fibers having superior cleanliness can be produced. Thus, the raw material is preferably formed of titanium alloy fibers produced by the molten metal extraction method.

The sintering process may be preferably performed by hot pressing sintering, hot isostatic pressing sintering, or spark plasma pressure sintering, which have a compressing mechanism and enable sintering in a vacuum or in an inert gas atmosphere. By heating to a predetermined temperature and compressing the nitrogen-containing mixed material, a sintered titanium alloy member containing few pores and nitrogen that is uniformly diffused can be obtained.

Furthermore, by hot plastic forming the sintered titanium alloy member, pores can be greatly decreased. Thus, titanium alloy member containing no pores or almost no pores and uniformly diffused nitrogen is obtained. It is desirable that heating temperature of the sintered titanium alloy member in the hot plastic forming process be in a range from 800 to 1200° C.

Since strain brought by the processing may become too large in a case in which the heating temperature during the hot plastic forming process is less than 800° C., crack may generate at the surface of the member or the sintered titanium alloy member during processing may be broken. On the other hand, in a case in which the heating temperature is more than 1200° C., coarse α phase may be deposited in grain boundary after processing caused by β phase coarsening during heating, or equiaxed structure may be formed by dynamic recrystallization depending on processing condition. Ductility may be greatly decreased if the coarse α phase is deposited. Furthermore, strain which has been accumulated may be lost if the equiaxed structure is formed, effect of work hardening may be lost, thereby deteriorating strength.

It is desirable that nitrogen is solid solved in a range from 0.02 to 0.13% in the titanium alloy member. Nitrogen is uniformly dispersed in condition of solid solution, thereby realizing high strength and high proof stress in the entirety and improving fatigue strength. However, the effect cannot be sufficiently obtained in a case of less than 0.02% of nitrogen content, and ductility may be greatly decreased thereby being brittle in a case of 0.13% of nitrogen content.

The hot plastic forming may be performed by forging, rolling, drawing, or extruding. The forging is preferably performed to form a member into a near net shape. The rolling is preferably performed to form a thin sheet member which will be formed into the shape of a product by subsequent press forming. By the drawing or the extruding, the sintered titanium alloy member is deformed and is provided with larger internal strain, whereby a more densified processed member having high strength and high proof stress can be obtained. The densified processed member does not or barely contains pores that can become origins of fractures in fatigue in which repeated stress is loaded, whereby high fatigue resistance is stably obtained.

By hot plastic forming the sintered titanium alloy member, a finely deformed structure made of an α-β phase is obtained. The finely deformed structure is work hardened by strain accumulation, and it has a great number of grain boundaries that are perpendicular or curved with respect to directions of crack growth, and thereby has a great effect for preventing crack growth by stopping and curving cracks. Accordingly, fatigue resistance is further improved. Thus, the titanium alloy member obtained after the hot plastic forming is preferably formed of the finely deformed structure for improving the fatigue resistance.

In particular, the finely deformed structure preferably has not less than 30% of "$GOS_{\geq 320}$". The GOS (Grain Orientation Spread) is calculated as the average misorientation among all pixels in a grain. The "$GOS_{\geq 3°}$" represents an area ratio of grains with not less than 3° of GOS to the entire observation visual field. When the "$GOS_{\geq 3°}$" is less than 30%, the structure is not sufficiently deformed, and thereby the above effects are not sufficiently obtained, and fatigue resistance decreases. Moreover, since pores having diameter more than 10 μm tend to be origins of fractures in fatigue, which occurs when repeated stress is loaded, the diameter of the pores is preferably less than 10 μm so as to reliably obtain high fatigue resistance.

Furthermore, in the present invention, it is desirable that 0.2% bending proof stress of the titanium alloy member obtained be not less than 1600 MPa.

The present invention also provides a titanium alloy member that can be obtained by the above-described production method, and the titanium alloy member contains finely deformed structure and contains nitrogen at 0.02 to 0.13 mass % in solid solution. Since not less than 0.02% of nitrogen diffuses by solid solution, the titanium alloy member of the present invention is strengthened overall and has high proof stress, whereby the fatigue resistance is improved.

The titanium alloy member of the present invention can be used for parts which must be reduced in weight, such as aircraft parts and automobile parts, and in particular, the titanium alloy member is suitably used for parts that should have high strength. The titanium alloy is superior in corrosion resistance and in biocompatibility, and therefore, the titanium alloy member is preferably used for biological implant devices. In particular, the titanium alloy member is more preferably used for biological implant devices that should have high strength because the benefit of its low weight is obtained to a high degree.

According to the present invention, a titanium alloy member that is made of an inexpensive α-β type titanium alloy having broad utility and has high proof stress and high strength from the surface to the entire interior portion can be provided.

BRIEF DESCRIPTION OF THE DRAWINGS

FIG. 1A is a schematic side sectional view of the overall apparatus, and FIG. 1B is a sectional view of a circumferential edge of a disk used in the apparatus.

FIG. 2A is a side view of the fiberizing apparatus and FIG. 2B is a partially enlarged view of the fiberizing apparatus.

Figure 1A:
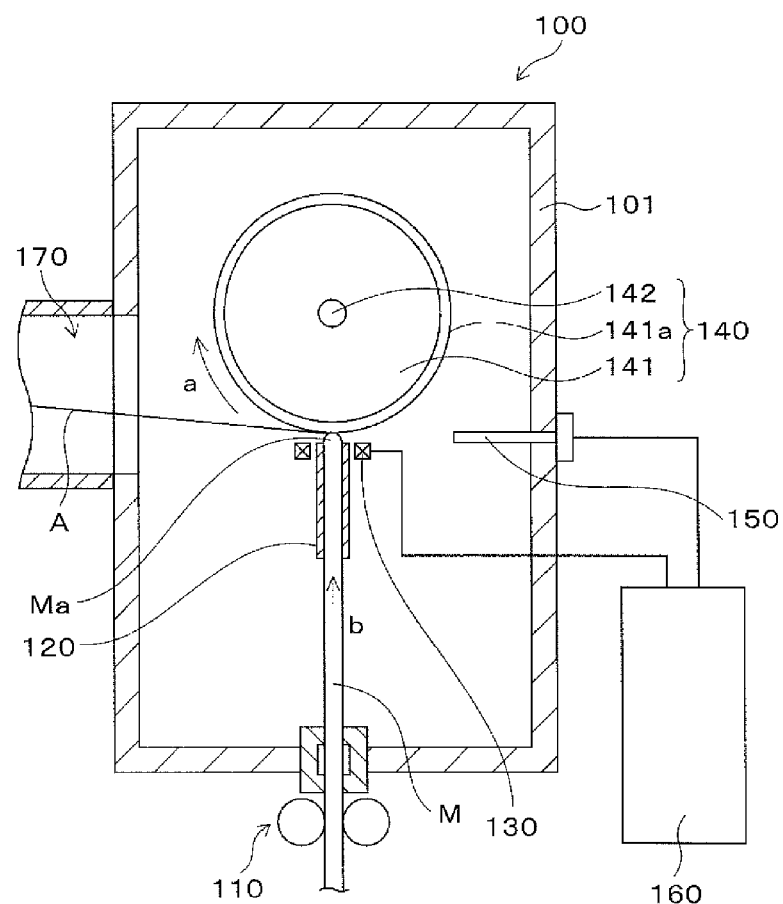
FIGS. 1A and 1B show a metal fiber producing apparatus used in an embodiment of the present invention.

EXPLANATION OF REFERENCE NUMERALS 100 denotes a metal fiber producing apparatus, 101 denotes a chamber, 110 denotes a material feeding portion, 120 denotes a material holding portion, 130 denotes a heating portion, 140 denotes a disk rotating portion, 141 denotes a disk, 141a denotes a circumferential edge, 142 denotes a rotating shaft, 150 denotes a temperature measuring portion, 160 denotes a high-frequency generating portion, 170 denotes a metal fiber receiving portion, 200 denotes a fiberizing apparatus, 210 denotes a material conveyer, 211 denotes a feed roller, 212 denotes a fiberizing mechanism, 213 denotes a conveyer, 214 denotes a belt, 300 denotes an extruding apparatus, 305 denotes an outer die, 310 denotes a container, 320 denotes a lower die, 330 denotes a die, 340 denotes a punch, 360 denotes a heater, A denotes a raw material, B denotes a nitrogen-containing raw material, A+B denotes a nitrogen-containing mixed material, C denotes a sintered titanium alloy member, M denotes a material, and Ma denotes a molten material.

EMBODIMENT OF THE INVENTION

A method for producing the titanium alloy member of the present invention will be specifically described. It should be noted that the apparatuses used in the following method are merely an embodiment, and other apparatuses may also be used.

(1) Preparing Step

Figure 1B:
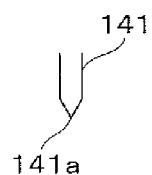

FIGS. 1A and 1B schematically show a metal fiber producing apparatus 100 for obtaining a raw material A (hereinafter called an "apparatus 100"). FIG. 1A is a schematic side sectional view of the overall apparatus 100, and FIG. 1B is a sectional view of a circumferential edge 141a of a disk 141 used in the apparatus 100. FIG. 1B is a side sectional view in a direction perpendicular to the plane of the paper of FIG. 1A.

The apparatus 100 is a metal fiber producing apparatus using a molten metal extraction method. In the apparatus 100, an upper end portion of a rod-shaped material M melts, and the molten material Ma contacts the circumferential edge 141a of the rotating disk 141. Then, a portion of the molten material Ma is extracted toward an approximately tangential direction of the circumference of the disk and is rapidly cooled, and thereby a titanium alloy fiber is formed as a raw material A. For example, an α-β type titanium alloy such as Ti-6Al-4V is used as a material M for a raw material A, and a raw material A having a diameter of 10 to 200 μm is produced. The diameter of the raw material A is not particularly limited and is appropriately selected according to the amount of nitrogen that should be contained in the titanium alloy member. For example, when a larger amount of nitrogen should be contained, the diameter of the raw material A may be thinner. In this case, the proportion of a nitrogen compound layer and/or a nitrogen solid solution layer which are formed by the nitriding can be increased with respect to the diameter.

As shown in FIG. 1A, the apparatus 100 includes a sealable chamber 101 containing a material feeding portion 110, a material holding portion 120, a heating portion 130, a disk rotating portion 140, a temperature measuring portion 150, a high-frequency generating portion 160, and a metal fiber receiving portion 170.

The chamber 101 is evacuated or is filled with an inert gas as an atmosphere so as to inhibit reaction of impurities such as oxygen and the molten material Ma. For example, an Ar (argon) gas can be used for the inert gas atmosphere. The material feeding portion 110 is located, for example, at the bottom of the chamber 101, feeds the material M toward the direction of the arrow "b" at a predetermined speed, and provides the material M to the material holding portion 120. The material holding portion 120 prevents movement of the molten material Ma toward a radial direction thereof and guides the material M to a suitable position of the disk rotating portion 140.

The material holding portion 120 is a water-cooled metal tubular member and is located below the disk 141 between the material feeding portion 110 and the metal fiber forming portion 140. The heating portion 130 is a high-frequency induction coil that generates magnetic flux for melting the upper end portion of the material M and forming the molten material Ma. As a material for the material holding portion 120, a material that has high thermal conductivity for cooling effect by a cooling water and is non-magnetic to avoid effects of the magnetic flux generated by the heating portion 130 is preferable. Copper or copper alloy is preferable as a material for the material holding portion 120 for practical use.

The disk rotating portion 140 produces a raw material A from the molten material Ma by the disk 141 which rotates around a rotating shaft 142. The disk 141 is made from, for example, copper or copper alloy having high thermal conductivity. As shown in FIG. 1B, a V-shaped circumferential edge 141a is formed on the circumferential portion of the disk 141.

The temperature measuring portion 150 measures the temperature of the molten material Ma. The high-frequency generating portion 160 supplies high-frequency current to the heating portion 130. The power of the high-frequency generating portion 160 is controlled based on the temperature of the molten material Ma, which is measured by the temperature measuring portion 150, and thereby the temperature of the molten material Ma is maintained constant. The metal fiber receiving portion 170 receives the raw material A which is formed by the metal fiber forming portion 140.

In the apparatus 100 constructed in this way, first, the material feeding portion 110 continually feeds the material M in the direction of the arrow "b", thereby supplying it to the material holding portion 120. The heating portion 130 melts the upper end portion of the material M by induction heating, thereby forming the molten material Ma. Then, the molten material Ma is continually fed to contact the circumferential edge 141a of the disk 141 rotating in the direction of the arrow "a", and a part thereof is extracted toward an approximately tangential direction of the circumference of the disk 141 and is rapidly cooled, whereby a raw material A is formed. The formed raw material A extends toward the approximately tangential direction of the circumference of the disk 141 and is received by the metal fiber receiving portion 170 which is located in the direction in which the raw material A extends.

(2) Nitriding Step

In the nitriding step, an aggregate of the raw material A produced in the preparing step is carried into a vacuum furnace, which is then evacuated and supplied with a nitrogen gas, and the raw material A is heated. In this case, an inert gas such as an argon gas may be supplied with the nitrogen gas for adjusting the density and the pressure of the nitrogen gas. The pressure and the temperature in the furnace and processing time are suitably selected according to amount of nitrogen which should be contained in a titanium alloy member.

If the temperature in the furnace is too low, a very long time is required to form a nitrogen compound layer and/or a nitrogen solid solution layer. If the temperature in the furnace is too high, the processing time is difficult to control because the reaction rate is high, and a thick nitrogen compound layer is readily formed. The thick nitrogen compound layer requires a very long time for diffusing nitrogen in a subsequent sintering step. Thus, the temperature in the furnace is preferably 600 to 1000° C. for practical production. By the nitriding step, a nitrogen-containing raw material B in which a very thin TiN compound layer and/or nitrogen solid solution layer is formed in a surface layer of the raw material A is produced.

(3) Mixing Step

Figure 2A:
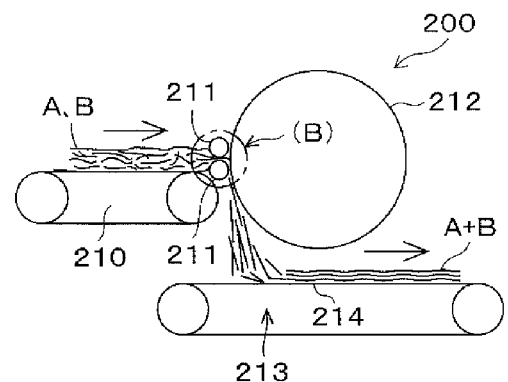
FIGS. 2A and 2B show a fiberizing apparatus used in an embodiment of the present invention.

The raw material A and the nitrogen-containing raw material B are mixed together with predetermined percentage according to amount of nitrogen which should be contained in a titanium alloy member. As a mixing means, for example, a fiberizing apparatus 200 shown in FIG. 2A is used. Appropriate amounts of an aggregation of the raw material A and an aggregation of the nitrogen-containing raw material B are supplied to a material conveyer 210 and are moved to the exit side. A feed roller 211 is located at the exit of the material conveyer 210. A fiberizing mechanism 212 is located outside of the feed roller 211.

Figure 2B:
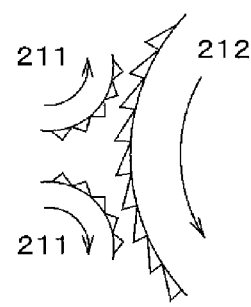

As shown FIG. 2B, the feed roller 211 includes numerous feeding teeth provided on the circumference thereof, and the feeding teeth bite and feed the raw material A and the nitrogen-containing raw material B. The fiberizing mechanism 212 includes numerous fiberizing teeth provided on the circumference thereof, and the fiberizing teeth comb a part of the raw material A and the nitrogen-containing raw material B, which are fed from the feed roller 211, and drop it on a belt 214 of a conveyer 213. In this condition, the raw material A and the nitrogen-containing raw material B are cut and mixed and are piled up on the belt 214 as an aggregation of random fibers without orientation in a cross section in a direction approximately perpendicular to the belt 214, whereby a nitrogen-containing mixed material A+B is formed. As a mixing means other than the fiberizing apparatus 200 shown in FIG. 2A, various means can be appropriately used. For example, unwoven fabric forming machines, such as of the card type and the aeration type, and mixing machines such as mixers and mills can be used.

(4) Sintering Step

The nitrogen-containing mixed material A+B is sintered by an apparatus that has a pressurizing mechanism and that can be evacuated or be purged with an inert gas. In the case of a vacuum HP (Hot Press) apparatus, a heating chamber is arranged in a vacuum vessel, and a mold is arranged within the heating chamber. In this case, a cylinder is provided at the upper side of the vacuum vessel, a press ram projected from the cylinder is vertically movable in the heating chamber, and an upper punch installed at the press ram is inserted into the mold. The nitrogen-containing mixed material A+B is charged into the mold of the vacuum HP apparatus as constructed above, the vacuum vessel is evacuated or purged with an inert gas, and the heating chamber is heated to a predetermined sintering temperature. Then, the nitrogen-containing mixed material A+B is compressed by the upper punch inserted into the mold, and is sintered.

The sintering should be performed in a vacuum or an inert atmosphere to avoid contamination by impurities such as oxygen from the atmosphere into a titanium alloy member. The sintering temperature is preferably 900° C. or more, the sintering time is preferably 30 minutes or more, and the pressure of pressing is preferably 10 MPa or more. By sintering the nitrogen-containing mixed material A+B in such conditions, a sintered titanium alloy member C containing few pores can be obtained. Nitrogen contained in the nitrogen-containing raw material B uniformly diffuses into the entire interior portion of the sintered titanium alloy member C by solid solution during the sintering. Thus, the formed sintered titanium alloy member C contains no nitrogen compounds or contains very few nitrogen compounds, and has a plate-like structure composed of an α-β phase.

(5) Hot Plastic Forming Step

Figure 3:
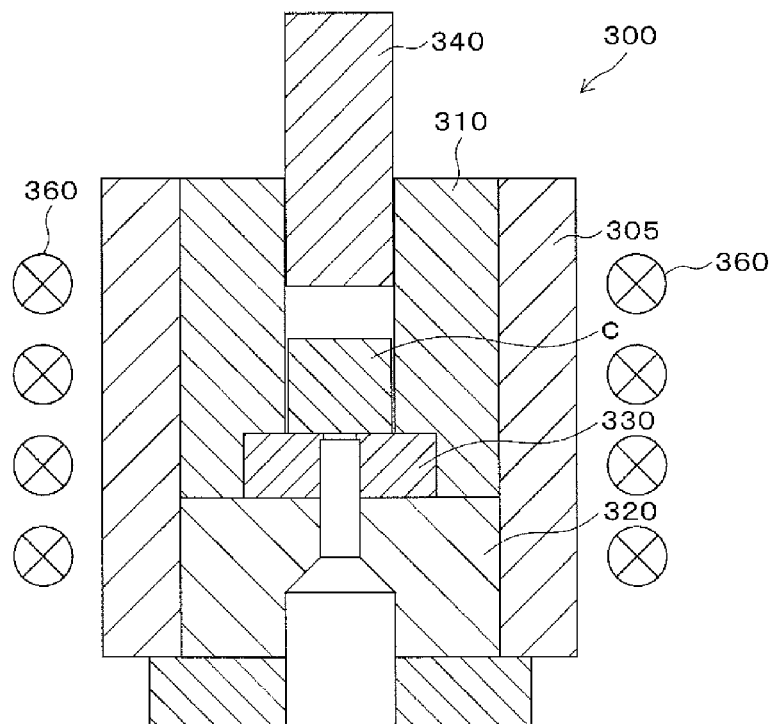
FIG. 3 is a side sectional view of an extruding apparatus used in an embodiment of the present invention.

The sintered titanium alloy member C can be subjected to hot plastic forming. The hot plastic forming is performed by, for example, an extruding apparatus shown in FIG. 3. The extruding apparatus 300 has an outer die 305 containing a tubular container 310, and a lower die 320 is coaxially arranged at an end side of the container 310. A die 330 is arranged between the container 310 and the lower die 320, and a punch 340 can be slidably inserted into the container 310. A heater 360 is arranged around the container 310.

The sintered titanium alloy member C is preliminarily heated by an outer furnace. After the sintered titanium alloy member C is charged into the container 310, the punch 340 moves down and compresses the sintered titanium alloy member C. The compressed sintered titanium alloy member C is extruded to the space inside the lower die 320 while being reduced in diameter by the die 330, whereby an extruded material is formed. The heating temperature of the sintered titanium alloy member C in the outer furnace may be 800 to 1200° C., the extrusion ratio may be 2 to 7, and the forward speed of the punch 340 may be 1 to 30 mm/second. By extruding the sintered titanium alloy member C in such conditions, all or almost all pores remaining after the sintering are removed, and a high strength and high proof stress processed member having a fine deformed structure composed of an α-β phase can be obtained.

The conditions such as the heating temperature and the extrusion ratio in the extruding have a complicated relationship with each other in conjunction with the material composition of the titanium alloy and the effects of the contained nitrogen, and they are suitably determined by theory, experience, and experiment. Although the fine deformed structure is obtained by setting the heating temperature and the extrusion ratio in this embodiment, an appropriate heating temperature and appropriate processing parameters should be set to obtain the fine deformed structure according to the processing method when a processing method other than the extruding is used.

Examples

The present invention will be described in detail by way of specific examples.

1. Production of Samples (1) Preparation of Raw Material (Preparing Step)

A raw material with an average wire diameter of 60 μm was produced from Ti-6Al-4V (corresponding to ASTM B348 Gr. 5) using the apparatus 100 shown in FIG. 1A.

(2) Preparation of Nitrogen-Containing Raw Material (Nitriding Step)

A part of the raw material was subjected to nitriding as follows. First, the raw material was carried into a vacuum furnace. After evacuating, a nitrogen gas was fed into the vacuum furnace, and the pressure in the furnace was set at 80 kPa. Then, the temperature in the furnace was increased to 800° C. and maintained for 1.5 hours to perform nitriding.

(3) Preparation of Nitrogen-Containing Mixed Material (Mixing Step)

The raw material and the nitrogen-containing raw material were supplied to the fiberizing apparatus 200 shown in FIGS. 2A and 2B and mixed together, whereby a nitrogen-containing mixed material was obtained. The weight percentage (Wf) of the mixed nitrogen-containing raw material is shown in Table 1.

(4) Preparation of Sintered Titanium Alloy Member (Sintering Step)

The nitrogen-containing mixed material was charged into a carbon mold, and a sintered titanium alloy member having a thickness of 28 mm was obtained by a vacuum HP apparatus. After the vacuum chamber was evacuated to the degree of vacuum of $1\times10^{-2}$ Pa or less and purged with an argon gas so as to be at 80 kPa, the sintering was performed at a temperature increasing rate of 10° C./minute, a sintering temperature of 1100° C., and a pressure of press of 40 MPa for 1.5 hours, and cooling was then performed in the furnace. The carbon mold and the nitrogen-containing mixed material as well as the sintered titanium alloy member which is a sintered body of the mixed material are reactive under the high temperature conditions described above. In view of this, a release plate as a liner made from $Al_2O_3$ (alumina, purity of 99.5% or more) was preliminarily installed to the carbon mold.

(5) Preparation of Titanium Alloy Member Sample (Hot Plastic Forming Step)

The sintered titanium alloy member was formed into a shape with a diameter of 25 mm and a height of 90 mm by machining and was heated in an outer furnace. Then, the sintered titanium alloy member was hot plastic formed by the extruding apparatus 300 shown in FIG. 3, whereby a processed titanium alloy member was prepared (Samples Nos. 101 to 125). The heating temperature ($T_E$) in the outer furnace was 700 to 1200° C., the temperature of the container was 300° C., the forward speed of the punch was 10 mm/second, and the extrusion ratio (R) was 1.5 to 10. The sintered titanium alloy member was preliminary applied with an antioxidizing lubricating agent (DeltaGlaze349 manufactured by Acheson Japan) before heating. The time from taking out the sintered titanium alloy member from the outer furnace to starting to advance the punch was approximately 30 seconds. The extruded titanium alloy member was water cooled right under the lower die.

The result of extruding is also shown in Table 1. In Table 1, "broken" means that the member was broken during extrusion and titanium alloy material which is an extruded material was not obtained, "rough/crack" means that extruded titanium alloy material in which surface roughness and/or cracking were observed was obtained, and "superior" means that superior titanium alloy member having no roughness and cracking was obtained. The samples of "superior" were further evaluated.

(7) Preparation of Comparative Sample

For comparison, a rod of an expanded material of Ti-6Al-4V (corresponding to ASTM B348 Gr. 5) was prepared as a comparative sample 10. In addition, this expanded material was subjected to the hot plastic forming with the same conditions as described above, whereby a comparative sample No. 11 was prepared. Result of extrusion of the comparative sample 11 is also shown in Table 1.

TABLE 1

| Sample | Wf (%) | $T_E$ (° C.) | R | Extrusion result |
|---|---|---|---|---|
| Sample 101 | 5 | 1100 | 4 | Superior |
| Sample 102 | 10 | 1100 | 4 | Superior |
| Sample 103 | 15 | 1100 | 4 | Superior |
| Sample 104 | 20 | 1100 | 4 | Superior |
| Sample 105 | 25 | 1100 | 4 | Superior |
| Sample 106 | 30 | 1100 | 4 | Superior |
| Sample 107 | 35 | 1100 | 4 | Superior |
| Sample 108 | 40 | 1100 | 4 | Superior |
| Sample 109 | 20 | 700 | 4 | Broken |
| Sample 110 | 20 | 750 | 4 | Rough/crack |
| Sample 111 | 20 | 800 | 4 | Superior |
| Sample 112 | 20 | 850 | 4 | Superior |
| Sample 113 | 20 | 900 | 4 | Superior |
| Sample 114 | 20 | 1000 | 4 | Superior |
| Sample 115 | 20 | 1150 | 4 | Superior |
| Sample 116 | 20 | 1200 | 4 | Superior |
| Sample 117 | 20 | 1100 | 1.5 | Superior |
| Sample 118 | 20 | 1100 | 2 | Superior |
| Sample 119 | 20 | 1100 | 3 | Superior |
| Sample 120 | 20 | 1100 | 5 | Superior |
| Sample 121 | 20 | 1100 | 6 | Superior |
| Sample 122 | 20 | 1100 | 7 | Superior |
| Sample 123 | 20 | 1100 | 8 | Rough/crack |
| Sample 124 | 20 | 1100 | 9 | Broken |
| Sample 125 | 20 | 1100 | 10 | Broken |
| Comparative sample 10 | — | — | — | — |
| Comparative sample 11 | — | 1100 | 4 | Superior |

2. Evaluation Items and Evaluation Methods

Evaluation items and evaluation methods will be described hereinafter. The evaluation results are shown in Table 2.

(1) Structure

Figure 4:
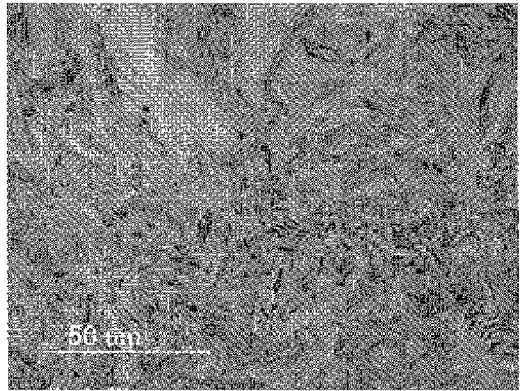
FIG. 4 shows photographs of structures of titanium alloy members in the Example.
Figure 4:
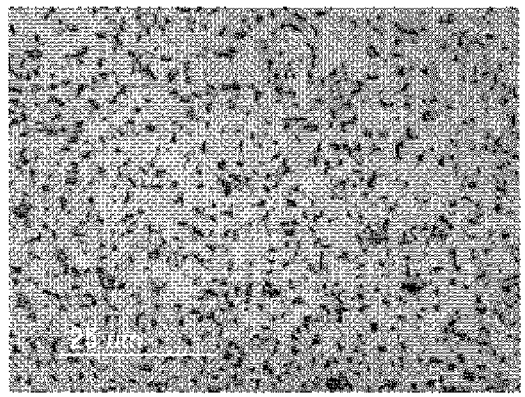
Figure 4:
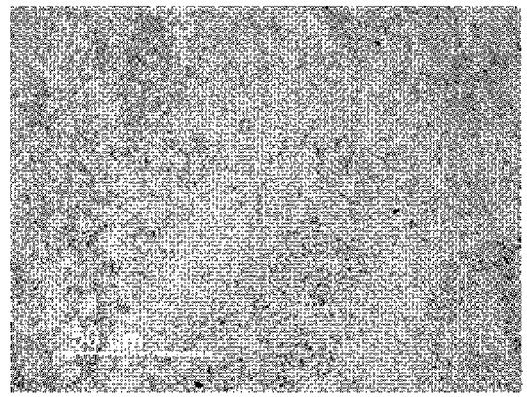

Each sample was cut into a suitable size and embedded in a resin so that the cross sectional structure perpendicular to the axial direction could be observed. Then, the embedded sample was mirror finished by mechanical polishing and was etched by an etching fluid (2 wt % of hydrofluoric acid and 4 wt % of nitric acid), and the structure was observed by an optical microscope (NIKON ME600). FIG. 4 shows typical microscope photographs of the samples. A fine deformed structure composed of an α-β phase is represented by the symbol "A" and an equiaxed structure composed of an α-β phase is represented by the symbol "B" in Table 2.

(2) Existence of TiN Compound Phase (TiN Phase)

The crystal structure was analyzed by an X-ray diffractometer (Rigaku X-ray Diffractometer RINT2000) using Cu tube target, and peak of TiN compound phase was observed.

(3) Porosity

Each sample was cut into a suitable size and embedded in a resin so that the cross sectional structure perpendicular to the axial direction could be observed. Then, the embedded sample was mirror finished by mechanical polishing. Then, pores were observed by a field-emission-type scanning electron microscope (FE-SEM, JSM-7000F, manufactured by JEOL). Magnification of observation was 100 times (visual field area 1.1 mm$^2$). The number of pores observed in the magnitude was counted at freely selected thirty positions per each sample, and the number of pores per unit area was calculated as porosity (porosity (number/mm$^2$)= number of all pores/(visual field area×30)).

(4) Amount of Nitrogen (N Amount)

Amount of nitrogen was measured by inert gas melting-thermal conductivity technique and solid state type infrared absorption method (LECO TC600).

(5) Area Ratio of Grains with not Less than 3° of Average Misorientation in Grain (GOS$_{≥3°}$)

A GOS (Grain Orientation Spread: An average misorientation among all pixels in a grain) map was formed by FE-SEM/EBSD (Electron Back Scatter Diffraction) method (JEOL JSM-7000F, TSL solutions OIM-Analysis Ver. 4.6) at 1000-times magnification. Then, an area ratio of grains with not less than 3° of GOS to the entire observation visual field (GOS$_{≥3°}$) was calculated.

(6) Hardness (HV)

Hardness of the vicinity of the surface and the center of each sample in a cross section perpendicular to the axial direction were measured by a Vickers hardness tester (FUTURE-TECH FM-600). The test load was 10 gf. The hardness of the vicinity of the surface was measured at 10 points at 1 mm below the outer circumferential surface and the center hardness was measured at 10 points at the center and the vicinity of the center of the cross section, and the averages were calculated.

(7) Bending Strength ($\sigma_b$), 0.2% Bending Proof Stress ($\sigma_{b0.2}$)

A three-point bending test was performed by a 300 kN universal testing machine (INSTRON 5586 type). The test piece had a width of 6 mm, a length of 17 mm, and a thickness of 1 mm, and the distance between fulcrums was 15 mm. An average of bending strength (maximum bending stress) and an average of 0.2% bending proof stress were calculated by testing three pieces of each sample at a rate of 6 mm/minute.

TABLE 2

| Sample | Wf (%) | $T_E$ (° C.) | R | Structure | TiN phase | Porosity (number/mm$^2$) | Nitrogen amount (mass %) | GOS$_{≥3°}$ (%) | HV Surface | HV Center | $\sigma_b$ (MPa) | $\sigma_{b0.2}$ (MPa) |
|---|---|---|---|---|---|---|---|---|---|---|---|---|
| Sample 101 | 5 | 1100 | 4 | A | Non | 0.00 | 0.022 | 42.2 | 379 | 369 | 2613 | 1611 |
| Sample 102 | 10 | 1100 | 4 | ↑ | ↑ | 0.00 | 0.034 | 38.4 | 377 | 372 | 2650 | 1702 |
| Sample 103 | 15 | 1100 | 4 | ↑ | ↑ | 0.00 | 0.053 | 34.1 | 379 | 379 | 2683 | 1778 |
| Sample 104 | 20 | 1100 | 4 | ↑ | ↑ | 0.00 | 0.075 | 38.6 | 390 | 394 | 2708 | 1832 |
| Sample 105 | 25 | 1100 | 4 | ↑ | ↑ | 0.00 | 0.089 | 35.8 | 410 | 414 | 2727 | 1853 |
| Sample 106 | 30 | 1100 | 4 | ↑ | ↑ | 0.00 | 0.105 | 41.8 | 424 | 421 | 2625 | 1890 |
| Sample 107 | 35 | 1100 | 4 | ↑ | ↑ | 0.00 | 0.122 | 45.7 | 440 | 435 | 2323 | 1910 |
| Sample 108 | 40 | 1100 | 4 | ↑ | ↑ | 0.00 | 0.138 | 49.9 | 445 | 454 | 2022 | Not reached |
| Sample 111 | 20 | 800 | 4 | ↑ | ↑ | 0.00 | 0.069 | 52.3 | 410 | 399 | 2780 | 1867 |
| Sample 112 | 20 | 850 | 4 | ↑ | ↑ | 0.00 | 0.077 | 48.7 | 388 | 389 | 2754 | 1861 |
| Sample 113 | 20 | 900 | 4 | ↑ | ↑ | 0.00 | 0.080 | 43.2 | 395 | 395 | 2736 | 1835 |
| Sample 114 | 20 | 1000 | 4 | ↑ | ↑ | 0.00 | 0.072 | 40.0 | 396 | 403 | 2711 | 1810 |
| Sample 104 | 20 | 1100 | 4 | ↑ | ↑ | 0.00 | 0.075 | 38.6 | 390 | 394 | 2708 | 1832 |
| Sample 115 | 20 | 1150 | 4 | ↑ | ↑ | 0.00 | 0.074 | 38.0 | 388 | 384 | 2715 | 1841 |
| Sample 116 | 20 | 1200 | 4 | ↑ | ↑ | 0.00 | 0.078 | 30.4 | 396 | 386 | 2635 | 1799 |
| Sample 117 | 20 | 1100 | 1.5 | ↑ | ↑ | 0.65 | 0.072 | 21.5 | 372 | 376 | 2311 | 1520 |
| Sample 118 | 20 | 1100 | 2 | ↑ | ↑ | 0.00 | 0.066 | 32.2 | 389 | 383 | 2321 | 1620 |
| Sample 119 | 20 | 1100 | 3 | ↑ | ↑ | 0.00 | 0.073 | 34.2 | 390 | 388 | 2554 | 1711 |
| Sample 104 | 20 | 1100 | 4 | ↑ | ↑ | 0.00 | 0.075 | 38.6 | 390 | 394 | 2708 | 1832 |
| Sample 120 | 20 | 1100 | 5 | ↑ | ↑ | 0.00 | 0.070 | 42.5 | 401 | 396 | 2716 | 1865 |
| Sample 121 | 20 | 1100 | 6 | ↑ | ↑ | 0.00 | 0.069 | 40.1 | 399 | 389 | 2782 | 1957 |
| Sample 122 | 20 | 1100 | 7 | ↑ | ↑ | 0.00 | 0.077 | 46.5 | 410 | 400 | 2770 | 1922 |
| C. Sample | — | — | — | B | ↑ | 0.00 | 0.005 | 1.3 | 312 | 308 | 1896 | 1023 |
| C. Sample | — | — | 4 | A | ↑ | 0.00 | 0.008 | 46.2 | 358 | 364 | 2640 | 1575 |

3. Results (1) Heating Temperature

Influence of heating temperature is obvious from the samples 104 and 109 to 116. It is understood that the titanium alloy member can be produced by setting the heating temperature of the sintered titanium alloy member at 750 to 1200° C. in the case in which the extrusion ratio of extrusion is 4, from Tables 1 and 2. Lower heating temperature is desirable in order to realize high strength and high proof stress since larger stein can be introduced. However, in the sample 110 in which heating temperature was 750° C., cracking was generated on the member surface since the strain induced was too large. Therefore, it is obvious that the heating temperature of the sintered titanium alloy member is desirably set at 800° C. or more. In a case in which the heating temperature was more than 1200° C., coarse α phase may be deposited at grain boundary, and equiaxed structure may be formed by dynamic recrystallization depending on an extrusion ratio condition. As a result, ductility and strength may be deteriorated.

However, from the samples Nos. 104 and 117 to 125, it is obvious that the titanium alloy member is difficult to be produced if the extrusion ratio is too large even in the case in which the heating temperature is 1100° C. Furthermore, it is understood that the titanium alloy member can be appropriately produced by setting the heating temperature at 1100° C. and the extrusion ratio at 4 even in the case in which nitrogen amount is varied, from the samples Nos. 101 to 108. As explained, the conditions such as the heating temperature and the extrusion ratio in the extruding have a complicated relationship with each other in conjunction with the material composition of the titanium alloy and the effects of the contained nitrogen. Therefore, in the titanium alloy member of the present invention, it is desirable that extrusion is performed with controlling the extrusion ratio at the heating temperature of 800 to 1200° C. in order to realize high strength and high proof stress.

(2) Structure

The samples Nos. 101 to 108, and 111 to 122 were subjected to the extruding and had a fine deformed structure composed of an α-β phase. FIG. 4 (picture 1, sample No. 104) shows an example of fine deformed structure. The comparative sample No. 11 was also subjected to the extruding and also had a fine deformed structure composed of an α-β phase as shown in FIG. 4 (picture 3, comparative sample No. 11). On the other hand, the comparative sample No. 10 is a generally available expanded material, and has an equiaxed structure composed of an α-β phase as shown in FIG. 4 (picture 2, comparative sample No. 10). Since titanium alloy has low workability, the alloy is typically processed by a hot processing to a final product shape. Therefore, the comparative sample No. 10 which is a commercially available expanded material is shown in FIG. 4 (picture 2, comparative sample No. 10).

(3) TiN Compound Phase

According to the results of the X-ray diffraction, the peaks of nitrogen compounds such as the TiN compound phase were not detected in all of the samples. It indicates that the contained nitrogen did not form nitrogen compounds and were solid solved in the matrix. Existence of nitrogen compounds having a great difference in hardness (or elastic strain) from the matrix is undesirable because the boundary between the nitrogen compound phase and the matrix tends to be origins of fractures and can thereby cause decrease in the fatigue strength. Therefore, the titanium alloy member of the present invention is suitable with respect to fatigue in which repeated stress is loaded, because there is no boundary between a nitrogen compound phase and the matrix, which makes a great difference in the hardness and tends to be an origin of fractures.

(4) Porosity

As a result of observation of the pores, there were not pores observed in the samples except for the sample No. 117. This result shows that the pores which slightly remained after sintering were extinguished by the extrusion processing, whereby there were no pores or almost no pores. The porosity was 0.65 number/mm$^2$ in the sample No. 117 in which the extrusion ratio was small and thus the pores remained, thereby deteriorating the 0.2% bending proof stress. In addition, as a result of observing the pores of the sample No. 117 in detail by a high magnitude, the diameter of the pores were 6.5 to 23.6 μm (the longer diameter was measured in a case in which pore is not circle), that is, the result indicates that there are no pores having diameter not less than 6.5 μm in the samples in which no pores were observed by the 100 times observation magnitude, except for the sample No. 117. A pore having diameter 10 μm or more may easily be an origin of fractures in fatigue in which repeated stress is loaded. Therefore, present invention is desirable for increasing fatigue strength since pores having diameter 6.5 vim or more do not exist.

(5) Amount of Nitrogen

Figure 5:
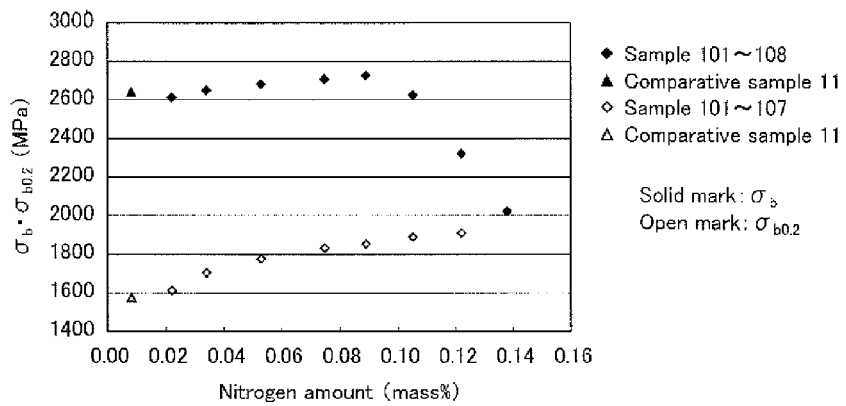
FIG. 5 shows a graph showing a relationship between amount of nitrogen and bending strength and 0.2% bending proof stress of titanium alloy members in the Example.

FIG. 5 is a graph showing a relationship of the amount of nitrogen and bending strength and 0.2% bending proof stress. The Sample No. 101 containing 0.022% of nitrogen had slightly less bending strength than the comparative sample No. 11. However, the Sample No. 101 had greater 0.2% bending proof stress than the comparative sample No. 11 and is suitable for a part to be used under conditions which cause fatigue, because it can be used under higher stresses. As the amount of nitrogen increased, the bending strength and the 0.2% bending proof stress increased until the amount of nitrogen was 0.089% as in the Sample No. 105. However, in the Sample No. 106 containing 0.105% of nitrogen, the 0.2% bending proof stress further increased, but the ductility decreased, whereby the bending strength decreased to the level of the comparative sample No. 11. This tendency observed when the amount of nitrogen was 0.105% or more increased with the increase in the amount of nitrogen, and the Sample No. 108 containing 0.138% of nitrogen broke before reaching the 0.2% bending proof stress. When the amount of nitrogen was less than 0.02%, the strength and the proof stress were not effectively improved compared with those of the comparative sample No. 11. Accordingly, the titanium alloy member of the present invention preferably contains 0.02 to 0.13% of nitrogen in solid solution.

(6) Area Ratio of Grains with not Less than 3° of Average Misorientation in Grain ($GOS_{\geq 3°}$)

Figure 6:
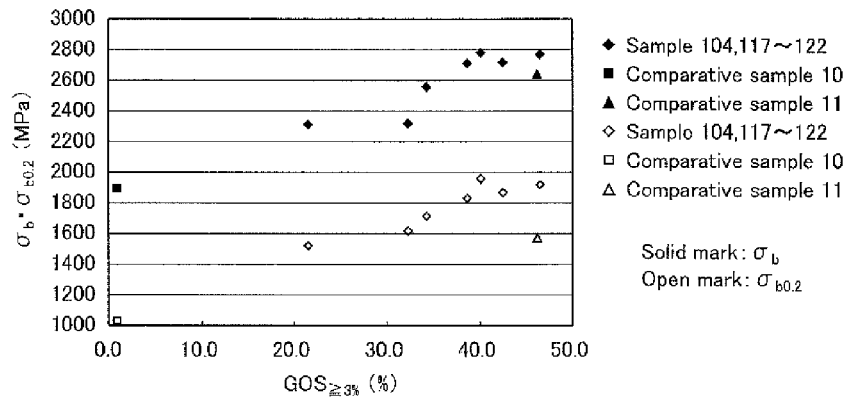
FIG. 6 shows a graph showing a relationship between area ratio of crystal grain ($GOS_{\geq 3°}$) and bending strength and 0.2% bending proof stress of titanium alloy members in the Example.

As shown by the results of the samples subjected to the extruding, the values of "$GOS_{\geq 3°}$" as a parameter for the amount of strain accumulation were much greater than those of the comparative sample No. 10, which had an equiaxed structure. This result suggests that the fine deformed structure is work hardened due to strain accumulation, and the fine deformed structure contains a great number of grain boundaries that are perpendicular or curved with respect to directions of crack growth, thereby having a great effect for preventing crack growth by stopping and curving cracks, whereby the fatigue resistance can be improved. Furthermore, as shown in the samples Nos. 104, 117 to 122 of Table 2, the $GOS_{\geq 3°}$ becomes larger as the extrusion ratio is larger, and the bending strength and the 0.2% bending proof stress, that is, fatigue resistance is improved more as the $GOS_{\geq 3°}$ becomes larger as is obvious from FIG. 6 which shows relationship between the $GOS_{\geq 3°}$ and the bending strength and the 0.2% bending proof stress. The $GOS_{\geq 3°}$ of a sample in which 0.2% bending proof stress of 1600 MPa or more was obtained, which was more than the comparative sample No. 11, was 30% or more.

(7) Hardness

Figure 7:
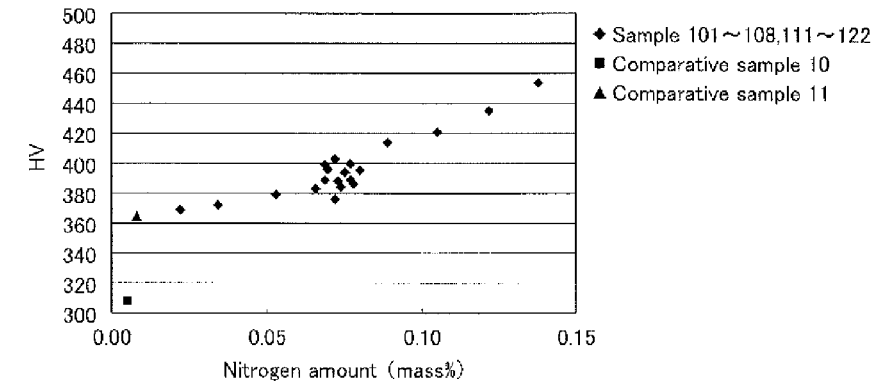
FIG. 7 shows a graph showing a relationship between amount of nitrogen and hardness of titanium alloy members in the Example.

As shown in Table 2, in all of the samples Nos. 101 to 108 and 111 to 122, the hardness of the surface and the hardness of the center were approximately the same. The samples had hardness that is equal to or greater than the hardness of the comparative sample No. 11 subjected to the extruding in the same manner. As shown in FIG. 7, there was a close relationship between the amount of nitrogen and the hardness, and the hardness improved in accordance with the increase in the amount of nitrogen. Thus, according to the present invention, the titanium alloy member can be greatly strengthened in the entirety at the interior portion, and a necessary degree of strength can be obtained.

The conditions in the sintering and the extruding are not limited to the conditions described in this Example and can be appropriately set in view of obtaining high strength and high proof stress. That is, the densified amount and the degree of diffusion of nitrogen in the sintering and the amount of strain introduced in the plastic forming greatly depend on complicated relationships such as the material composition, the temperature, and the processing rate, and can be determined by appropriately setting conditions based on theory, experience, and experiment.

The titanium alloy material of the present invention is applicable for materials used for aircraft and automobiles required to be light in weight and have high strength, and materials for biological implant devices.

The invention claimed is:

1. A titanium alloy member having a fine deformed structure including curved grains and containing 0.02 to 0.13 mass % of nitrogen in solid solution, GOS$_{\geq 3°}$ of the titanium alloy member is 30% or more, when an average misorientation among all pixels in each grain by FE-SEM/EBSD (Electron Back Scatter Diffraction) method is represented by GOS (Grain Orientation Spread) and an area ratio of grains with not less than 3° of the GOS to the entire observation visual field is represented by the GOS$_{\geq 3°}$, the titanium alloy member has 0.2% bending proof stress of 1702 MPa or higher, and a bending strength of 2321 MPa or higher, wherein diameter of pores in the titanium alloy member having the fine deformed structure is less than 10 μm, and the fine deformed structure is constructed without an α coarse phase and without a β coarse phase.

2. The titanium alloy member according to claim 1, wherein the titanium alloy member is made from an α-β type titanium alloy.

3. The titanium alloy member according to claim 1, wherein the titanium alloy member is produced by the following method:

preparing a raw material made of titanium alloy;

nitriding the raw material to form a nitrogen-containing raw material by generating a nitrogen compound layer and/or a nitrogen solid solution layer in a surface layer of the raw material;

mixing the raw material and the nitrogen-containing raw material to yield a nitrogen-containing mixed material;

sintering the nitrogen-containing mixed material to obtain a sintered titanium alloy member by bonding the material together and uniformly diffusing nitrogen in solid solution from the nitrogen-containing raw material to the entire interior portion of the sintered titanium alloy member; and hot plastic forming the sintered titanium alloy member.

4. A biological implant device comprising the titanium alloy member of claim 1.

5. The titanium alloy member according to claim 1, which has a bending strength of 2650 MPa or higher.

6. The titanium alloy member according to claim 1, wherein the GOS$_{\geq 3°}$ of the titanium alloy member is 40% or more.

7. The titanium alloy member according to claim 1, which has a 0.2% bending proof stress of 1810 MPa or higher.

8. The titanium alloy member according to claim 1, wherein the fine deformed structure is formed by hot plastic working without dynamic recrystallization occurring.

9. The titanium alloy member according to claim 1, wherein the amount of nitrogen in solid solution is 0.053 to 0.13 mass %.

10. A method for producing a titanium alloy member of claim 1, comprising:

preparing a raw material made of titanium alloy;

nitriding the raw material to form a nitrogen-containing raw material by generating a nitrogen compound layer and/or a nitrogen solid solution layer in a surface layer of the raw material;

mixing the raw material and the nitrogen-containing raw material to yield a nitrogen-containing mixed material;

sintering the nitrogen-containing mixed material to obtain a sintered titanium alloy member by bonding the material together and uniformly diffusing nitrogen in solid solution from the nitrogen-containing raw material to the entire interior portion of the sintered titanium alloy member; and hot plastic forming the sintered titanium alloy member.

11. The method for producing the titanium alloy member according to claim 10, wherein the raw material is made of an α-β type titanium alloy.

12. The method for producing the titanium alloy member according to claim 10, wherein the raw material is a titanium alloy fiber produced by a molten metal extraction method.

13. The method for producing the titanium alloy member according to claim 10, wherein the heating temperature of the sintered titanium alloy member in the hot plastic forming is in a range of 800 to 1200° C.

14. The method for producing the titanium alloy member according to claim 10, wherein the sintering is performed by one of hot pressing sintering, hot isostatic pressing sintering, and spark plasma pressure sintering.

* * * * *